United States Patent [19]

Rosen

[11] 4,345,340
[45] Aug. 24, 1982

[54] STENT FOR MITRAL/TRICUSPID HEART VALVE

[75] Inventor: Jonathan J. Rosen, Fountain Valley, Calif.

[73] Assignee: Vascor, Inc., Anaheim, Calif.

[21] Appl. No.: 261,392

[22] Filed: May 7, 1981

[51] Int. Cl.³ .............................................. A61F 1/22
[52] U.S. Cl. ........................................................ 3/1.5
[58] Field of Search ........................................ 3/1.5, 1

[56] References Cited

U.S. PATENT DOCUMENTS

| | | | |
|---|---|---|---|
| 3,448,465 | 7/1969 | Pierce et al. | 3/1.5 |
| 3,503,079 | 3/1970 | Smith | 3/1.5 |
| 3,570,014 | 3/1971 | Hancock | 3/1.5 |
| 3,755,823 | 9/1973 | Hancock | 3/1.5 |
| 3,839,741 | 10/1974 | Haller | 3/1.5 |
| 3,983,581 | 10/1976 | Angell et al. | 3/1.5 |
| 4,035,849 | 7/1977 | Angell et al. | 3/1.5 |
| 4,084,268 | 4/1978 | Ionescu et al. | 3/1.5 |
| 4,106,129 | 8/1978 | Carpentier et al. | 3/1.5 |
| 4,172,295 | 10/1979 | Batten | 3/1.5 |
| 4,222,126 | 9/1979 | Boretos et al. | 3/1.5 |

*Primary Examiner*—Ronald L. Frinks
*Attorney, Agent, or Firm*—Wayne R. Eberhardt

[57] ABSTRACT

A plastic stent for a prosthetic trileaflet heart valve consisting of a cylindrical body section terminating at one end in three apical, commissure posts, and at the other end, in an outward-extending flange. The flange is provided with an interrupted channel encircling the base of the cylindrical section. An optional metal ring may be mounted adjacent the flange and spaced from the base of the cylindrical section. A cloth cover is secured to the stent by stitching directly through the flange in the area of reduced thickness resulting from the interrupted channel.

16 Claims, 7 Drawing Figures

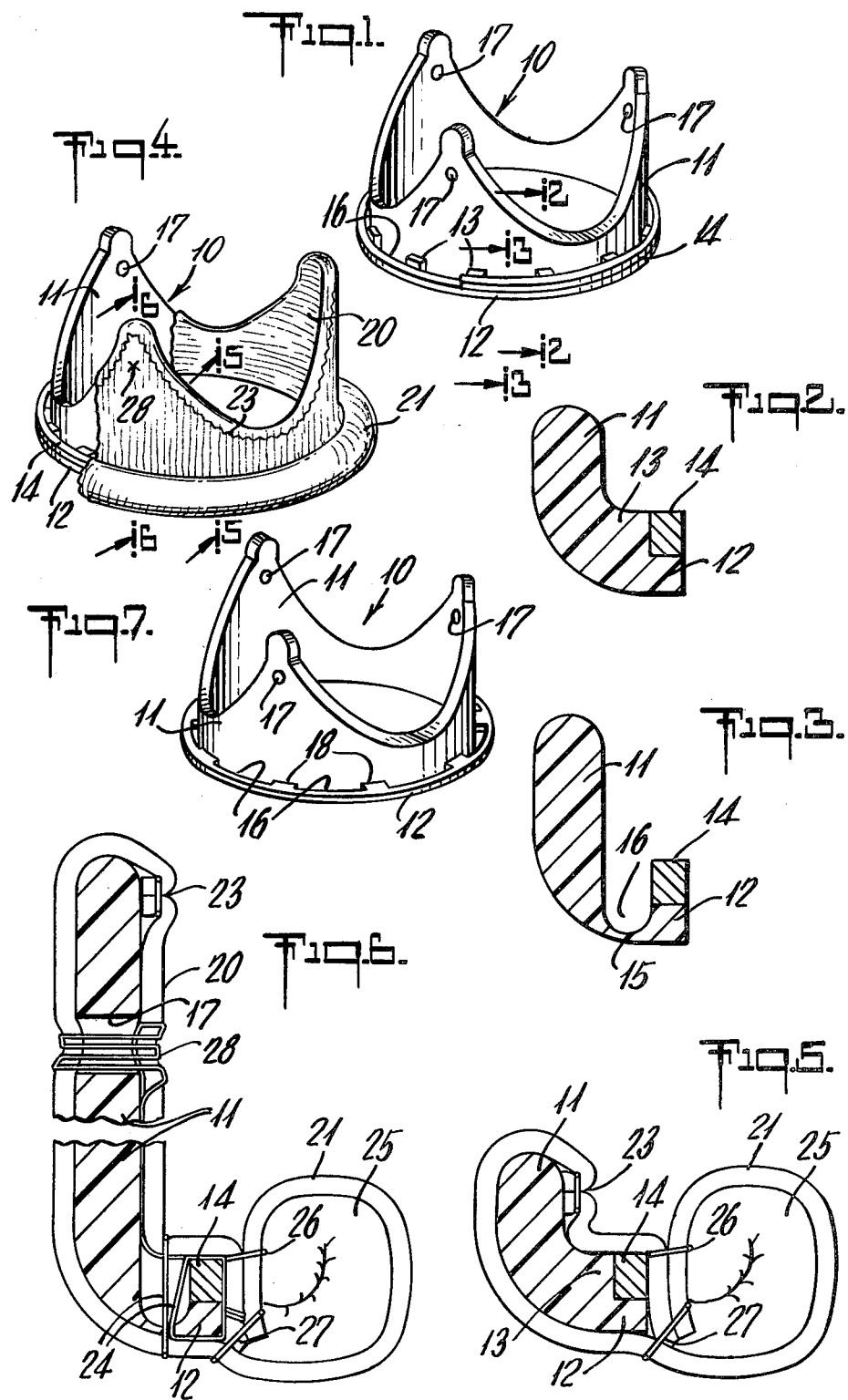

STENT FOR MITRAL/TRICUSPID HEART VALVE

BACKGROUND OF THE INVENTION

1. Field of the Invention

This invention relates to a framework or stent for mounting a trileaflet heart valve constructed of natural or synthetic materials, particularly for mitral or tricuspid valve replacement.

2. Description of Prior Art

Frame-mounted, trileaflet heart valves have been widely used for many years as a prosthetic replacement for defective mitral and tricuspid valves in humans. Natural tissue valves have been constructed by mounting gluteraldehyde-fixed porcine heart valves in a suitable framework as described, for example, in U.S. Pat. Nos. 3,570,014, 3,755,823, 3,983,581 and 4,035,849. Similar trileaflet valves have been constructed from autologous and hemologous fascia lata and dura matter, and from heterologous pericardium mounted in a suitable framework as described, for example, in U.S. Pat. Nos. 4,084,268 and 4,172,295.

More recently, efforts have been directed to the development of totally synthetic trileaflet heart valves constructed from tubes and films of biocompatible polymers such as polyurethane. Such valves are also mounted in a framework as described, for example, in U.S. Pat. No. 4,222,126.

Valve stents of the prior art have been constructed of noncorrosive metals such as stainless steel and of plastic such as polypropylene or polyethylene. Plastic stents for porcine valves as described in U.S. Pat. Nos. 3,570,014 and 3,755,823 have an intricate design which requires fabrication by machining from solid polymer at great expense. Plastic stents as described in U.S. Pat. Nos. 3,983,581 and 4,035,849 are of a simpler design and may be formed by injection molding. While such stents are less expensive than the machined stents, the cloth cover can only be attached to the stent with some difficulty by heat lamination.

It is accordingly an object of the present invention to provide an improved stent for mounting a porcine heart valve.

It is another object of this invention to provide a stent for mounting a trileaflet heart valve wherein the leaflets are constructed of natural or synthetic sheet materials.

It is a further object of this invention to provide a stent for a prosthetic heart valve intended for use in the mitral or tricuspid position.

It is a yet further object of this invention to provide an improved heart valve stent which may be injection-molded and still permit a cloth cover to be attached by stitching.

These and other objects of the present invention will be apparent from the ensuing description and claims.

SUMMARY OF THE INVENTION

This invention is directed to an improved design and construction of a heart valve stent particularly adapted for use in constructing a trileaflet heart valve of natural or synthetic materials for mitral or tricuspid valve replacement. The stent itself is injection-molded of any suitable, biocompatible, polymeric material such as polypropylene or polyethylene. The stent is comprised of a short cylindrical body section terminating at one end in a flange extending radially outward to form the base of the stent, and at the other end, in a scalloped configuration defining three circumferentially-spaced and axially-extending apical, commissure posts interconnected by valleys.

The cylindrical portion of the stent, including the commissure posts, has a generally uniform thickness throughout. The flange has a lesser thickness than the cylindrical section, and, in addition, is provided with an annulus of reduced thickness forming a channel adjacent the base of the cylindrical section. The flange is readily pierced by a surgical needle in the area of reduced thickness resulting from the channel which permits a cloth cover to be attached to the stent by stitching directly through the flange. Since the sewing thread actually pierces the flange of the stent rather than merely being looped around an arm or strut or passing through pre-existing holes as in prior art designs, there is no possibility of the threads slipping or the cloth cover being displaced relative to the stent during the stitching procedure.

The base of the stent may be circumferentially reinforced or made radiopaque, if desired, with a metal ring fitted about the cylindrical section adjacent the flange. In this event, there are provided a series of ring spacers extending radially from the base of the cylinder toward the edge of the flange. The ring is coextensive with the outer edge of the flange and encircles the base of the stent in a spaced relationship from the wall of the cylindrical section. When the cloth cover and sewing cushion are attached to the stent, the ring is secured in place by sewing threads which loop over the ring and pass through the flange.

DRAWINGS

FIG. 1 is a view in perspective of the heart valve stent of the present invention with the metal ring shown in partial view for clarity of illustration.

FIG. 2 is a view in cross section of the stent of FIG. 1 taken along line 2—2.

FIG. 3 is another view in cross section of the stent of FIG. 1 taken along line 3—3.

FIG. 4 is a view in perspective of a covered stent of FIG. 1 with the cloth cover and sewing cushion shown in partial view.

FIG. 5 is a view in cross section of the stent of FIG. 4 taken along line 5—5 corresponding to the cross-sectional view of FIG. 2.

FIG. 6 is a view in cross section of the stent of FIG. 4 taken along line 6—6 through a commissure post of the stent.

FIG. 7 is a view in perspective of a heart valve stent of the present invention without the optional metal ring.

DESCRIPTION OF INVENTION

Referring now to FIG. 1, there is illustrated a plastic stent 10 according to the present invention, including an optional metal ring 14. The stent consists of a cylindrical body 11 terminating at one end in three axially-extending commissure posts interconnected by valleys and defining a circumferentially-scalloped configuration. The opposite, or base end, of the cylindrical section terminates in an outwardly-extending flange 12 which includes channel 16 encircling the base of the cylindrical body. The channel is interrupted at regular intervals by ring spacers 13 extending radially from the cylindrical body toward the periphery of the flange. The annular edge of the flange beyond the spacers defines a ledge adapted to receive the metal ring 14 as best illustrated in FIG. 2 which is a view of the stent in cross section through a ring spacer. FIG. 3 is a view in cross section through a channel portion of the flange and illustrates the spacing between the metal ring and the body of the stent.

The stent of FIG. 1 is prepared for use in mounting a heart valve by adding a cloth cover and a sewing cushion as illustrated in FIGS. 4 through 6. FIG. 4 is a view in perspective of the stent of FIG. 1 with the cloth cover and sewing cushion illustrated in partial section. Cloth cover 20 is constructed of an inner section and an outer section joined at seam 23 which is positioned on the outer surface of the stent to avoid contact with the leaflets of the valve. The cloth cover is secured to the commissure posts by stitching 28 through hole 17 as illustrated in FIG. 6.

The inner section of the cloth cover is brought through the base of the stent around the bottom of the flange, and stitched to the outer section of cloth cover at 27 as illustrated in FIGS. 5 and 6. Stitching 24 extending through the channel portion of the flange secures the outer cloth at the base of the stent body and also secures the metal ring on the flange.

The fabric from the inner cover extends beyond the flange to encircle sewing cushion 25 which may be a washer of an elastomeric material such as silicone rubber or a torus formed from a rolled or folded fabric tube. The edge of the inner cover section is sewn to the outer cover section at 26, and the covered stent is then ready for mounting of the valve in accordance with conventional procedures.

The interrupted channel in the flange around the base of the stent body is an essential feature of the present invention in regard to both functional and economic considerations. The channel permits the cloth cover to be secured to the stent at the base of the body by stitching in a positive and reliable manner. The base of the channel provides support and reinforcement for the stitching and the cloth covering the bottom of the flange. Stitching through the base of the channel assures the stability of the stitch and cloth covering. Thus, the solid base of the flange and the interrupted channel encircling the body of the stent provide definite functional advantages. The economic advantage of the stent resides in its ability to be injection-molded. Many stents of the prior art which utilize open rails or struts must be fabricated by machining from solid blocks of polymer at great expense.

The stents of the present invention are preferably injection-molded of polypropylene or other suitable biocompatible thermoplastic polymeric material. Polypropylene is particularly preferred because it is readily molded, has good strength, and has a moderate degree of flexibility which is desirable to relieve stresses on the stent and the valve material during use. Other suitable materials include Delrin polymer (a polyformaldehyde of greater than 15,000 molecular weight sold by DuPont), Lexan polymer (a polycarbonate), nylon polymer (a hexamethylene diamine-adipic acid polymer) and high density polyethylene.

Valve stents may be molded in accordance with conventional injection molding techniques. Holes 17 in the commissure posts may be molded, but are preferably drilled and deburred in a separate operation. The molded stents are desirably annealed to relieve internal stress and subsequently polished and inspected before covering with cloth. Polypropylene stents may be suitably annealed by heating in an oven at about 90° C. for 20 minutes.

While the preceding description has been directed to a stent which incorporates a metal ring, this ring is optional as explained above. If the ring is to be omitted, ring spacers 13 are also eliminated to the extent that they extend above the surface of the flange as illustrated in FIG. 7. In FIG. 7, channel 16 is interrupted by a plurality of ribs 18 representing the full thickness of the flange and extending radially through the channel at regularly spaced intervals. Such ribs are desirable for reinforcing the flange which would otherwise be significantly weakened by the channel. If the metal ring is to be omitted, it may also be desirable to increase the thickness of the flange section to increase rigidity at the base of the stent.

The ribs and/or ring spacers interrupting the channel are preferably equiangularly spaced around the base of the stent body at 15° to 60° intervals, and preferably, at 30° intervals resulting in 12 ribs.

Typical stents for use in the mitral and tricuspid positions in humans have a nominal inside diameter of 23 to 31 mm. When molded of polypropylene, the thickness of the body of the stent is suitably at least about 1.0 mm, and preferably from about 1.0 to 1.5 mm; the flange at least about 0.5 mm, and preferably from about 0.5 to 1.0 mm; and the base of the channel less than about 0.2 mm, and preferably from about 0.1 to 0.15 mm. The flange is preferably at least about 2.0 mm wide, while the channel is preferably at least 1.0 mm wide. The annular portion of the flange extending beyond the channel and ring spacers is suitably about 1.0 mm wide to accommodate the metal reinforcing ring which is typically 1.5 mm high by 1.0 mm thick. The valve is proportioned approximately according to its nominal size with the maximum axial dimension of the apical, commissure posts being approximately equal to the inside radius of the cylindrical section, and the minimum axial dimension of the valleys between commissure posts being approximately 20% of the maximum axial dimension. The drilled hole in each commissure post is suitably about 0.9 mm in diameter.

The stents of the present invention can be used with good results to mount heart valves of natural or synthetic materials. Natural materials include, without limitation, standard porcine heart valves, modified porcine heart valves as where the leaflet with the septal shelf is replaced with a leaflet from another valve, and natural tissue valves wherein the three cusps of the valve are formed from three separate pieces of pericardial or fascia lata tissue. Synthetic materials include, without limitation, rubberized fabrics, polyurethane film, and one-piece molded polyurethane valves. Rubberized fabric and polyurethane film are utilized in valve construction by forming the three cusps of the valve from separate pieces of material or from a single tubular section. Conventional construction procedures in mounting the valve on the stent may be followed in all cases.

I claim:

1. A stent for a trileaflet heart valve comprising
   a body portion of a cylindrical section terminating at one end in three circumferentially-spaced commissure posts and at the other end in a flange extending radially outward from the base of said cylindrical section;
   said flange including an annulus of reduced thickness defining a channel adjacent the base of said cylindrical section;

said channel being interrupted by a plurality of spaced, radially-extending, reinforcing ribs traversing said channel.

2. The stent of claim 1 wherein said reinforcing ribs are equiangularly spaced at 15° to 60° intervals.

3. The stent of claim 1 wherein said reinforcing ribs are equiangularly spaced at 30° intervals.

4. The stent of claim 1 wherein said commissure posts define three apical portions interconnected by valleys in a scalloped configuration around the circumference of the cylindrical section.

5. The stent of claim 1 fabricated of polypropylene.

6. The stent of claim 5 wherein the full thickness of the flange is at least about 0.5 mm.

7. The stent of claim 6 wherein the area of reduced thickness of said flange is less than about 0.2 mm.

8. The stent of claim 5 wherein the thickness of the cylindrical section is at least about 1.0 mm.

9. The stent of claim 1 wherein the flange is at least about 2.0 mm wide.

10. The stent of claim 9 wherein the channel is at least about 1.0 mm wide.

11. A stent comprising a body portion of a cylindrical section terminating at one end in three circumferentially-spaced commissure posts and at the other end in a flange extending radially outward from the base of said cylindrical section;
   a ring concentric with said flange and spaced from said cylindrical section;
   a plurality of ring-spacing means extending radially from said cylindrical section adjacent said flange;
   said flange including an annulus of reduced thickness defining a channel adjacent the base of said cylindrical section;
   said channel being interrupted by said ring-spacing means extending through said channel.

12. The stent of claim 11 wherein said ring-spacing means are equiangularly spaced at 15° to 60° intervals.

13. The stent of claim 11 wherein said ring-spacing means are equiangularly spaced at 30° intervals.

14. The stent of claim 11 wherein the outer surface of said ring is coextensive with the outer edge of said flange.

15. The stent of claims 1 or 11 additionally including a sewing cushion and cloth cover secured to said stent by stitches passing through the flange in the area of reduced thickness resulting from said channel.

16. The stent of claim 15 wherein said cloth cover additionally encloses said sewing cushion, and said sewing cushion is secured to said stent as an extension of said flange.

* * * * *